(12) United States Patent
Shinoda et al.

(10) Patent No.: US 8,035,815 B2
(45) Date of Patent: Oct. 11, 2011

(54) OPTICAL DETECTION METHOD AND OPTICAL DETECTION APPARATUS FOR A FINE PARTICLE

(75) Inventors: Masataka Shinoda, Tokyo (JP); Shingo Imanishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 251 days.

(21) Appl. No.: 12/258,075

(22) Filed: Oct. 24, 2008

(65) Prior Publication Data

US 2009/0108214 A1 Apr. 30, 2009

(30) Foreign Application Priority Data

Oct. 26, 2007 (JP) ................................ P2007-278907

(51) Int. Cl.
*G01N 21/00* (2006.01)
(52) U.S. Cl. ... 356/339; 356/336; 356/337; 369/112.01; 369/112.23; 369/112.24
(58) Field of Classification Search .................. 356/336, 356/337, 339; 369/112.01, 112.23, 112.24, 369/44.23; 378/117, 143
See application file for complete search history.

(56) References Cited

U.S. PATENT DOCUMENTS

| | | | | |
|---|---|---|---|---|
| 4,906,094 A * | 3/1990 | Ashida | ........................... | 356/336 |
| 5,576,852 A * | 11/1996 | Sawada et al. | ................. | 358/475 |
| 5,991,360 A * | 11/1999 | Matsui et al. | ................... | 378/119 |
| 6,449,042 B1 * | 9/2002 | Hamann | ........................ | 356/339 |
| 6,573,992 B1 * | 6/2003 | Drake | ............................ | 356/338 |
| 6,580,504 B1 * | 6/2003 | Ortyn et al. | .................... | 356/338 |
| 6,707,551 B2 * | 3/2004 | Ortyn et al. | .................... | 356/338 |
| 6,778,724 B2 * | 8/2004 | Wang et al. | ...................... | 385/16 |
| 6,819,421 B1 * | 11/2004 | Mead et al. | .................... | 356/338 |
| 6,947,136 B2 * | 9/2005 | Ortyn et al. | .................... | 356/338 |
| 7,057,724 B1 * | 6/2006 | Mead et al. | .................... | 356/343 |
| 7,072,038 B2 * | 7/2006 | Quist et al. | ..................... | 356/338 |
| 7,170,601 B2 * | 1/2007 | Matsuda | ....................... | 356/336 |
| 7,180,833 B2 * | 2/2007 | Takeda et al. | .............. | 369/44.23 |
| 7,317,668 B2 * | 1/2008 | Takeda et al. | .............. | 369/44.23 |
| 7,352,461 B2 * | 4/2008 | Saito et al. | ..................... | 356/337 |
| 7,471,394 B2 * | 12/2008 | Padmanabhan et al. | ....... | 356/365 |
| 7,782,512 B2 * | 8/2010 | Shinoda | ..................... | 359/196.1 |
| 2004/0047270 A1 * | 3/2004 | Takeda et al. | ............. | 369/112.24 |
| 2007/0104074 A1 * | 5/2007 | Takeda et al. | ............. | 369/112.23 |
| 2010/0020321 A1 * | 1/2010 | Furuki et al. | ................... | 356/337 |

FOREIGN PATENT DOCUMENTS

| | | |
|---|---|---|
| JP | 2003-304867 | 10/2003 |
| JP | 2007-46947 | 2/2007 |

* cited by examiner

*Primary Examiner* — David A Vanore
(74) *Attorney, Agent, or Firm* — Finnegan, Henderson, Farabow, Garrett & Dunner, LLP

(57) ABSTRACT

Disclosed herein is an optical detection method and optical detection apparatus, the apparatus including: a light irradiation section configured to irradiate a laser beam upon one of fine particles which are successively fed in a flow path; and a light detection section configured to detect fluorescent light and/or scattered light generated from any of the fine particles upon which the laser beam is irradiated; the method including the steps of: irradiating a laser beam upon one of fine particles which are successively fed in a flow path; and detecting fluorescent light and/or scattered light generated from the fine particle; wherein the laser beam being formed as a pulse laser beam whose pulse intensity is modulated such that one laser beam or two or more laser beams having different wavelengths are irradiated by a plural number of times upon one fine particle with the intensity varied.

16 Claims, 12 Drawing Sheets

OPTICAL DETECTION METHOD AND OPTICAL DETECTION APPARATUS FOR A FINE PARTICLE

CROSS REFERENCES TO RELATED APPLICATIONS

The present invention contains subject matter related to Japanese Patent Application JP 2007-278907 filed in the Japan Patent Office on Oct. 26, 2007, the entire contents of which being incorporated herein by reference.

BACKGROUND OF THE INVENTION

1. Field of the Invention

This invention relates to an optical detection method and an optical detection apparatus for individually identifying fine particles such as cells or micro beads. More specifically, the present invention relates to an optical detection method and an optical detection apparatus wherein the type of a fine particle is identified from fluorescent light or scattered light generated from the fine particle when a laser beam of a particular wavelength is irradiated upon the fine particle.

2. Description of the Related Art

Generally, where it is intended to identify a living body-related small particle such as a cell, a microorganism or a ribosome, an optical detection method which uses a flow cytometry or flow cytometer is used as disclosed, for example, in Hiromitsu NAKAUCHI, "Cellular Engineering Separate Volume, Experiment Protocol Series, Master Flow cytometry", Shujunsha Co. Ltd., the second edition, Aug. 31, 2006 (hereinafter referred to as Non-Patent Document 1). The flow cytometry is a method of irradiating a laser beam of a particular wavelength on one of fine particles which are successively fed in a row in a flow path and detecting fluorescent light or scattered light generated from the fine particle to discriminate a plurality of fine particles one by one.

In particular, in the flow cell, a laminar flow is formed from sample liquid which includes fine particles of an object of detection and sheath liquid which flows around the sample liquid. Further, a very small pressure difference is applied between the sample liquid and the sheath liquid to arrange a plurality of fine particles included in the sample liquid into a row. If, in this state, a laser beam is irradiated upon the flow cell, then the fine particles pass one by one crossing the laser beam. At this time, fluorescent light and/or scattered light excited by the laser light and generated from each fine particle is detected using an electro-optical detector.

Then, the detected light is converted into an electric signal and into a numerical value to carry out statistic analysis thereby to decide the type, size, structure and so forth of each fine particle. It is to be noted that, if each of fine particles of an object of detection is qualified with a plurality of fluorescent dyes, then even if an optical filter is used to separate the detected light for individual wavelength bands, fluorescent light from a fluorescent dye which is not a target fluorescent dye sometimes leaks into a detector different from the detector for the target fluorescent dye. Therefore, in a detection method in related art, in order to obtain only data from object fluorescent light, fluorescent light correction of subtracting an overlap of fluorescent light is usually carried out.

Further, with the flow cytometry, since the type, size, structure and so forth of fine particles can be identified individually and a plurality of parameters can be analyzed simultaneously, even where sample liquid includes a plurality of kinds of fine particles, only necessary fine particles can be dispensed rapidly and with certainty.

Also a flow cytometer which guides, in order to make it possible to detect a plurality of fluorescent lights generated from a fine particle qualified with a plurality of fluorescent dyes, laser beams of wavelengths different from each other along the same incoming light path so as to be irradiated upon the fine particle has been proposed in the past. A flow cytometer of the type is disclosed in Japanese Patent Laid-Open No. 2007-046947 (hereinafter referred to as Patent Document 1). FIG. 12 schematically shows a configuration of the flow cytometer in related art disclosed in Patent Document 1. Referring to FIG. 12, the flow cytometer 101 includes a flow system 102 for arraying cells qualified with fluorescent dyes into one array in the flow cell, and an optical system 103 for irradiating a plurality of laser beams of different wavelengths from each other upon the cells to detect detection object light such as scattered light and fluorescent light. The flow cytometer 101 further includes a signal processing apparatus 104 for controlling and processing an electric signal relating to the scattered light and the fluorescent light outputted from the optical system 103.

In the related-art flow cytometer 101, a plurality of laser beams having different wavelengths from each other are irradiated in a predetermined period and in different phases from each other from light sources 106a, 106b and 106c. The laser beams are guided to the same incoming light path and condensed on a cell 105 by a light guide member 107. Consequently, even where a plurality of laser beams are irradiated upon a cell labeled with a plurality of fluorescent dyes, one incoming light path can be used. Therefore, a plurality of fluorescent lights emitted from a cell can be detected without setting delay time.

Further, also a method has been proposed wherein, in order to dispense live cells which can be utilized for regenerative medicine, interplanting and so forth, object cells are separated and dispensed without carrying out fluorescent labeling wherein a probe such as an antibody to which a fluorescent dye is coupled is used. The method is disclosed in Japanese Patent Laid-Open No. 2003-304867 (hereinafter referred to as Patent Document 2). In the method disclosed in Patent Document 2, forwardly scattered light and backwardly scattered light emitted from a cell are detected, and detection values of the cell are displayed as position information on a two-dimensional screen to identify the size and the structure of the cell.

SUMMARY OF THE INVENTION

However, the detection methods and detection apparatus in related art described above have the following problems. In particular, the first problem of the related-art detection methods resides in that, if a dispersion occurs with the intensity of fluorescent light or scattered light generated from fine particles, then the accuracy in fluorescent light-correction described above and data analysis which is carried out based on a result of the fluorescent correction degrades.

For example, if detected luminance levels of fluorescent light or scattered light indicate a difference by more than three digits, then where the method disclosed in Patent Document 1 mentioned hereinabove is used for detection, a signal from a comparatively low luminance level is covered with a noise level, but a signal from a comparatively high luminance level is saturated. This problem is remarkable particularly where only one control voltage can be set for a plurality of anodes or photo-detectors.

Therefore, in the related art, where fluorescent light or scattered light having a high luminance level is detected, the intensity of the laser beam used as excitation light and the sensitivity of the photo-detector such as a PMT (Photo-Multiplier Tube) are set to values with which no saturation of the signal level occurs. This improves the accuracy in analysis of fluorescent light or scattered light having a high luminance level. However, since the level of an output waveform of a signal from fluorescent light or scattered light of a low luminance level further decreases, the analysis itself of the fluorescent light output signal may become difficult.

The second problem of the related-art detection methods resides in that laser beam irradiation sometimes damages fine particles or degenerates fine particles due to a temperature rise. Further, the third problem of the related-art detection methods is that, when the temperature is high, a fluorescent dye qualifying fine particles is left off the surface of the fine particles and, when the light intensity is high, the fine particles are faded. The problems are liable to occur particularly where two or more laser beans are irradiated and where the fine particle of an object of detection is a cell.

Meanwhile, the method disclosed in Patent Document 2 is directed to dispensation of live cells and contemplates prevention of deterioration of cells caused by coupling of a fluorescent dye. Thus, the method does not take an influence of a laser beam into consideration. Therefore, it is supposed that a laser beam is irradiated upon cells by a method similar to the related-art method. Accordingly, the method disclosed in Patent Document 2 fails to prevent damage to and deterioration of fine particles by a laser beam.

Therefore, it is desirable to provide an optical detection method and an optical detection apparatus for a fine particle which can achieve fluorescent light correction and data analysis of high accuracy and detection of high reliability even where a plurality of fluorescent lights or scattered lights which exhibit a great difference in luminance level thereamong are to be detected and besides can reduce damage to and degeneration of fine particles by a laser beam.

According to an embodiment of the present invention, there is provided an optical detection method including the steps of irradiating a laser beam upon one of fine particles which are successively fed in a flow path, and detecting fluorescent light and/or scattered light generated from the fine particle, the laser beam being formed as a pulse laser beam whose pulse intensity is modulated such that one laser beam or two or more laser beams having different wavelengths are irradiated by a plural number of times upon one fine particle with the intensity thereof varied.

In the optical detection method, a plurality of detection signals having output levels different from each other for individual wavelengths are obtained, and consequently, a signal of an appropriate level is obtained upon one of the plural number of times of laser beam irradiation. Therefore, even if the intensity of fluorescent light and scattered light generated from a fine particle of an object of detection exhibits a great difference among different fine particles or among different fluorescent dyes, detection of high accuracy can be anticipated even if an irradiation condition of the laser beam or the sensitivity of a detector is not adjusted individually.

The optical detection method may be configured such that, where the flow speed of the fine particles is represented by x (m/second), the spot diameter of the laser beam by y (m), the number of times of modulation of the laser beam by w (times) and the number of wavelengths of the laser beam by n, the pulse width p (second) of the laser beam satisfies the following expression (1):

$$p < \frac{y}{x \times (w+1) \times n} \quad (1)$$

It is to be noted that the shape of the spot of the laser beam may be any shape such as a circular shape, an elliptical shape, a square shape or a rectangular shape, and where the spot shape is any other than a circular shape, the diameter y in the expression (1) above is given as a distance of the spot in a direction in which the fine particle passes.

The optical detection method may be configured such that the detected fluorescent light and/or scattered light is normalized based on the intensity of the laser beam. In this instance, the type or state of the fine particle may be identified from the normalized value.

The optical detection method may be configured such that two or more laser beams having different wavelengths from each other are irradiated upon the fine particle with the pulse intensity thereof modulated and with the phases thereof displaced from each other, and the fluorescent light or scattered light generated from the fine particle is detected for each of the wavelengths of the laser beams. In the optical detection method, only a light signal originating from a single excitation laser light can be detected, and therefore, the fluorescent light correction is facilitated in comparison with an alternative case wherein a plurality of laser beams are irradiated simultaneously.

In this instance, the optical detection method may be configured such that the fine particles are in a form qualified with two or more different fluorescent dyes, and fluorescent light or scattered light detected when one of the laser beams is irradiated is analyzed by inverse matrix analysis wherein a reference spectrum of any one of the fluorescent dyes which is not excited by the laser beam is set to zero. In the optical detection method, numerical value calculation in the inverse matrix analysis for fluorescent light correction is simplified, and the processing time can be reduced.

The optical detection method may be configured such that the laser beam is an ultrashort pulse laser beam. In the optical detection method, damage to the fine particle of an object of detection can be further reduced and the fine particle becomes less liable to be heated.

In this instance, the optical detection method may further include a step of detecting a temperature and/or a light intensity with which fine particles of an object of detection are destroyed in advance, at least one of conditions of an irradiation intensity, irradiation time, an irradiation waveform, a pulse duration, a phase, a pulse width and a pulse shape of the pulse laser beam being adjusted in response to a result of the detection. The pulse duration here is a ratio of the pulse width with respect to the cycle.

According to another embodiment of the present invention, there is provided an optical detection apparatus including a light irradiation section configured to irradiate a laser beam upon one of fine particles which are successively fed in a flow path, and a light detection section configured to detect fluorescent light and/or scattered light generated from any of the fine particles upon which the laser beam is irradiated, the light irradiation section irradiating the laser beam as a pulse laser beam while modulating the pulse intensity of the laser beam such that one laser beam or two or more laser beams having different wavelengths are irradiated by a plural number of times upon one fine particle with the intensity thereof varied.

The optical detection apparatus may be configured such that, where the flow speed of the fine particles is represented by x (m/second), the spot diameter of the laser beam by y (m), the number of times of modulation of the laser beam by w (times) and the number of wavelengths of the laser beam by n, the pulse width p (second) of the laser beam satisfies the expression (1) given hereinabove.

The optical detection apparatus may further include a data processing section configured to normalize the detected fluorescent light and/or scattered light based on the intensity of the laser beam. In this instance, the type or state of the fine particle may be identified from the normalized value.

The optical detection apparatus may be configured such that the light irradiation section irradiates two or more laser beams having different wavelengths from each other upon the fine particle with the pulse intensity thereof modulated and with the phases thereof displaced from each other, and the light detection section detects the fluorescent light or scattered light generated from the fine particle for each of the wavelengths of the laser beams.

In this instance, the optical detection apparatus may be configured such that, where the fine particles are in a form qualified with two or more different fluorescent dyes, fluorescent light or scattered light detected when one of the laser beams is irradiated is analyzed by inverse matrix analysis wherein a reference spectrum of any one of the fluorescent dyes which is not excited by the laser beam is set to zero.

The laser beam may be an ultrashort pulse laser beam. In the optical detection apparatus, damage to the fine particle of an object of detection can be further reduced and the fine particle becomes less liable to be heated.

In this instance, the optical detection apparatus may further include a laser beam control section configured to adjust, based on data detected in advance of a temperature and/or a light intensity with which fine particles of an object of detection detected are destroyed, at least one of conditions of an irradiation intensity, irradiation time, an irradiation waveform, a pulse duration, a phase, a pulse width and a pulse shape of the pulse laser beam.

In the optical detection method and the optical detection apparatus, the fine particles which are an object of detection may be cells or micro beads.

With the optical detection method and the optical detection apparatus, since the laser beam is formed as a pulse laser beam, damage to and deterioration of the fine particle by the laser beam can be reduced. Further, since the laser beam is irradiated while the pulse intensity thereof is modulated, a plurality of detection signals having different output levels from each other for individual wavelengths are obtained. Therefore, detection of high accuracy and superior reliability can be implement even where a plurality of fluorescent lights or scattered lights which exhibit a great difference in luminance level thereamong are to be detected.

DETAILED DESCRIPTION OF THE PREFERRED EMBODIMENTS

Figure 1:
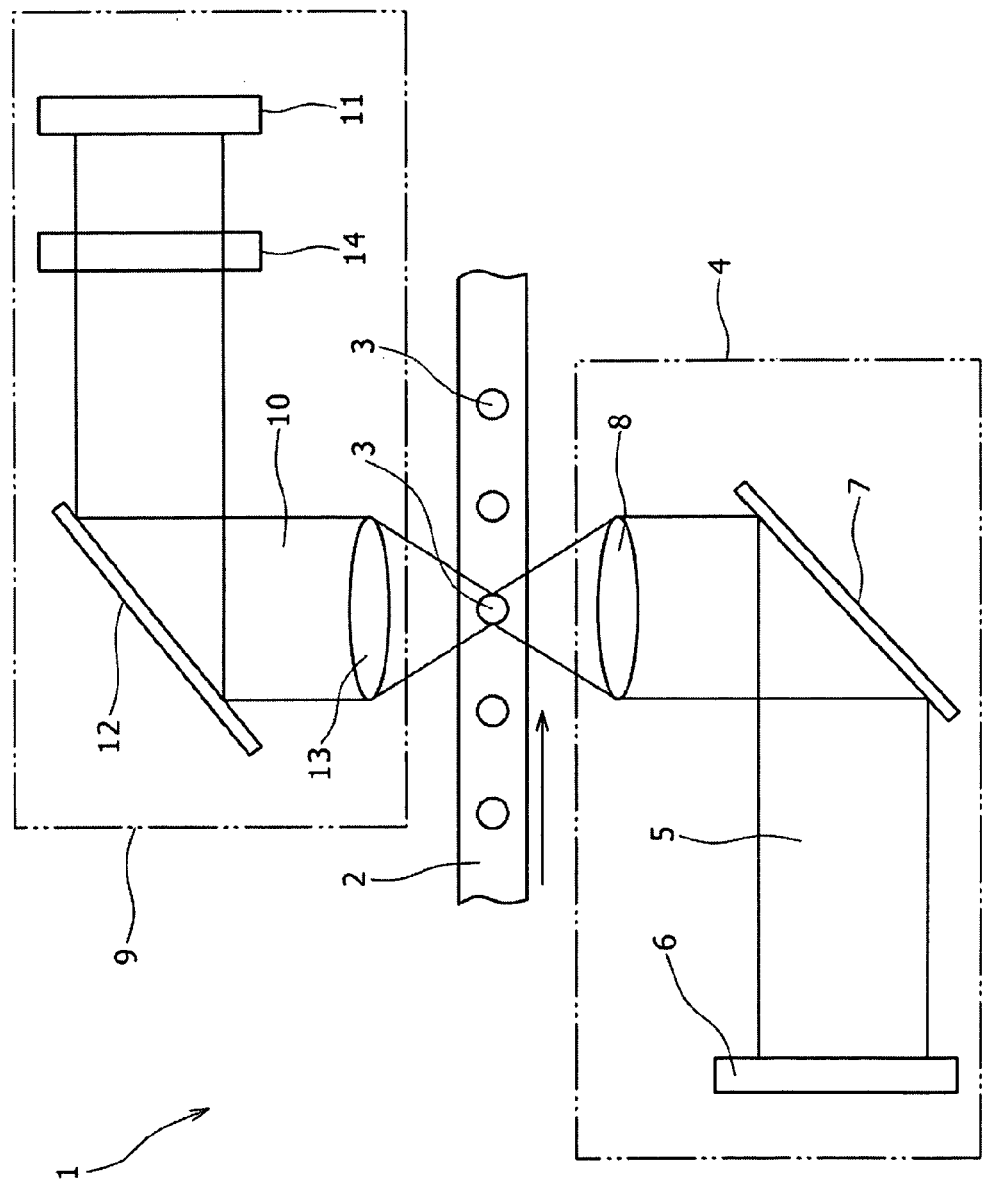
FIG. 1 is a schematic view showing a general configuration of an optical detection apparatus according to a first embodiment of the present invention.

First, an optical detection apparatus according to a first embodiment of the present invention is described. FIG. 1 schematically shows a configuration of the optical detection apparatus of the first embodiment. Referring to FIG. 1, the optical detection apparatus 1 shown includes a light irradiation section 4 for irradiating a laser beam 5 upon one of fine particles 3 which flow in a row in a flow path 2, and a detection section 9 for detecting fluorescent light and/or scattered light 10 generated from a fine particle 3 upon which the laser beam 5 is irradiated.

The light irradiation section 4 of the optical detection apparatus 1 includes, for example, a laser oscillator 6, a mirror 7, a condensing lens 8 and so forth and may be configured such that the laser beam 5 emitted from the laser oscillator 6 and reflected toward the flow path 2 by the mirror 7 is condensed by the condensing lens 8 and irradiated upon one fine particle 3.

The laser oscillator 6 used in the optical detection apparatus 1 in the present embodiment may be formed, for example, from a solid-state laser such as a YAG (Yttrium Aluminium Garnet) laser, a semiconductor laser, or a femtosecond laser, but need not necessarily be formed from the lasers mentioned. In other words, any laser may be suitably selected in response to the contents of detection and so forth only if it can emit a pulse laser beam while it modulates the pulse intensity.

Meanwhile, the detection section 9 of the optical detection apparatus 1 includes an light detection device 11 such as, for example, a CCD (Charge Coupled Device) detector or a PMT (Photo-Multiplier Tube) detector, a spectralizing element 14, a mirror 12 and a condensing lens 13. The detection section 9 may be configured such that the fluorescent light and/or scattered light 10 emitted from the fine particle 3 is condensed by the condensing lens 13 and reflected toward the light detection device 11 by the mirror 12 and then introduced to the light detection device 11 through the spectralizing element 14. Then, for example, where fluorescent light is to be detected, in the detection section 9, incoming fluorescent light is spectralized by a diffraction grating or the like to measure a fluorescent light spectrum.

The optical detection apparatus 1 of the present embodiment can be used, for example, as a flow cytometry or a bead assembly apparatus.

Now, operation of the optical detection apparatus 1 of the present embodiment having the configuration described above, that is, a method of optically detecting a fine particle 3 such as a cell or a micro bead using the optical detection apparatus 1, is described. It is to be noted that a fine particle 3 which is determined as a target of detection in the detection method of the present embodiment may be qualified with a plurality of fluorescent dyes.

Figure 2:
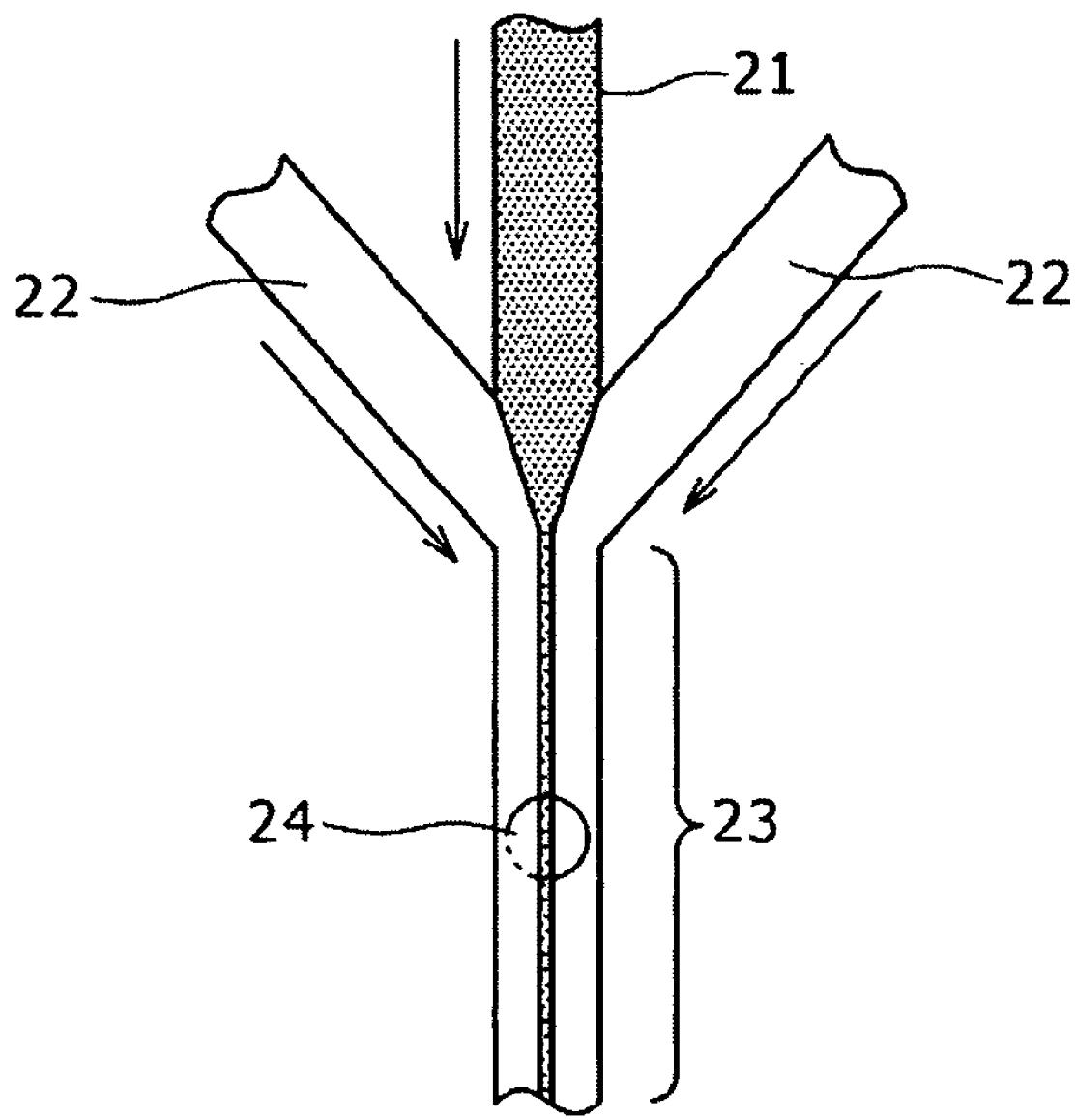
FIG. 2 is a view schematically illustrating a feeding process of a fine particle.

FIG. 2 schematically shows a feeding process of a fine particle 3. In the detection method of the present embodiment, the laser beam 5 is irradiated from the light irradiation section 4 upon one of the fine particles which are successively fed in a row in the flow path 2. According to a method of arranging the fine particles 3 in a row in the flow path 2, a laminar flow is formed from sample liquid 21 including the fine particles of a target of detection and sheath liquid 22 flowing around the sample liquid 21, for example, as seen in FIG. 2. Further, a very small pressure difference is provided between the sample liquid 21 and the sheath liquid 22 to arrange the fine particles 3 included in the sample liquid 21 so as to be lined up. In this instance, by irradiating the laser beam 5 upon a laminar flow portion 23, then even where a plurality of fine particles 3 are included in the sample liquid 21, the laser beam 5 can be irradiated upon the fine particles 3 one by one.

Then, in the detection method of the present embodiment, the laser beam 5 to be irradiated from the light irradiation section 4 is formed as a pulse beam, and the pulse intensity of the pulse beam is modulated such that one laser beam or two or more laser beams of different wavelengths are irradiated by a plural number of times upon one fine particle 3 while varying the intensity thereof.

The irradiation of the laser beam 5 whose laser intensity is modulated must be completed while the fine particle 3 passes a laser spot 24. Therefore, the pulse width p (second) of each laser beam 5 where n (n is a natural number equal to or greater than 1) laser beams of different wavelengths are irradiated is preferably set so as to satisfy the following expression (2):

$$p < \frac{y}{x \times (w+1) \times n} \quad (2)$$

where x is the speed (m/sec) at which the fine particle 3 is fed in the flow path 2, y the spot diameter (m) of the laser beam 5, and w is the number of times of modulation of the laser beam 5 and is equal to or greater than 1.

By setting the pulse width p (second) of the laser beam 5 within a range of the expression (2) given above, a pulse laser beam in an intensity-modulated form can be irradiated upon a fine particle 3 of a target of detection with certainty by one or more times for each intensity.

Then, in the detection method of the present embodiment, the fluorescent light and/or scattered light 10 emitted from a fine particle 3 in response to the laser beam 5 is detected by the light detection device 11. At this time, the sensitivity of the light detection device 11 provided in the detection section 9 is kept in a fixed state.

In contrast, in the detection method disclosed in Patent Document 1, the dispersion of a detection value is corrected by keeping the intensity of a laser beam fixed while adjusting the application voltage to the PMT, that is, the sensitivity of a PMT serving as a photo-detector. In this instance, the application voltage to the PMT must be varied at a high speed, and there is a problem that this is technically difficult. In contrast, with the detection method of the present embodiment, since the sensitivity of the light detection device 11 is kept fixed while the pulse intensity is varied, pulse intensity modulation can be carried out readily by varying the injection current for the laser beam at a high speed. Particularly where a semiconductor laser is used as the laser oscillator 6, the pulse width, pulse intensity and pulse shape of the laser beam 5 can be varied at a very high speed within a range from several MHz to several hundreds MHz.

Figure 3:
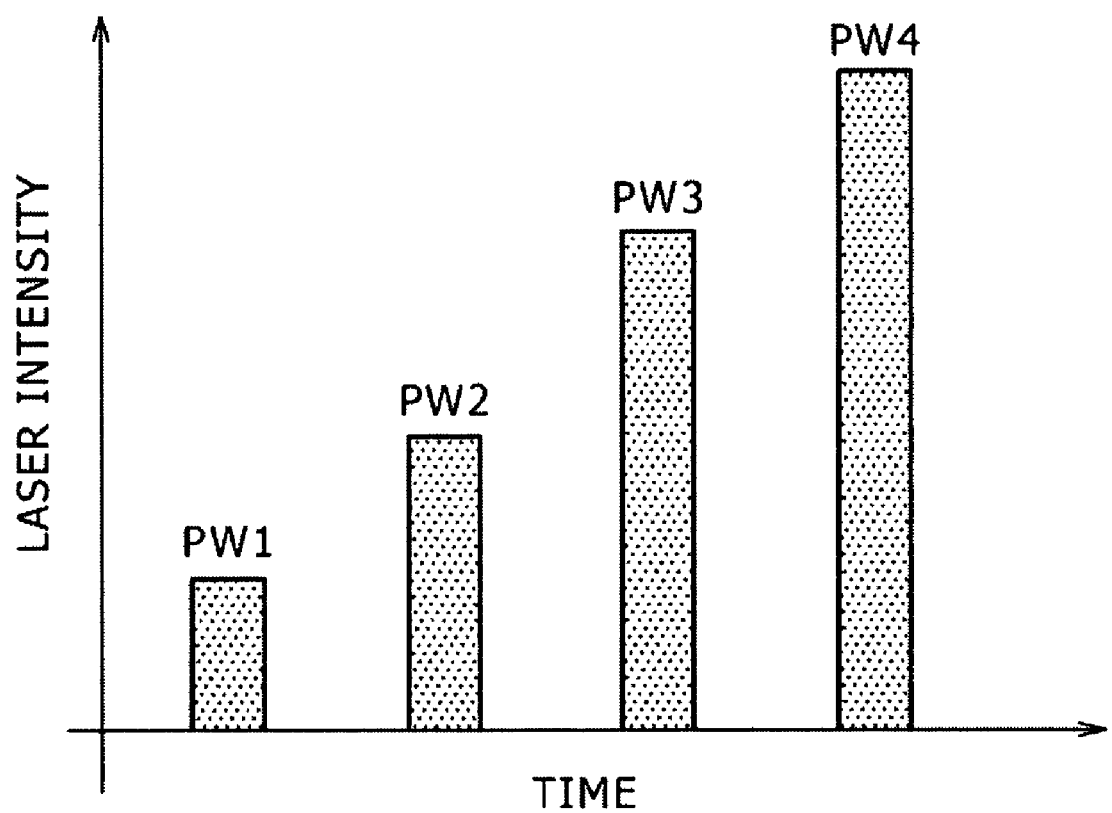
FIG. 3 is a graph illustrating an example of an irradiation pattern of laser beams.

An example of an irradiation pattern of the laser beam 5 is illustrated in FIG. 3 wherein the axis of abscissa indicates the time and the axis of ordinate indicates the intensity. Meanwhile, detection vectors obtained when a laser beam is irradiated in the pattern illustrated in FIG. 3 are illustrated in FIGS. 4A to 4D wherein the axis of abscissa indicates the wavelength and the axis of ordinate indicates the output power. In particular, FIGS. 4A, 4B, 4C and 4D illustrate detection spectra when the laser intensity is Pw1, Pw2, Pw3 and Pw4, respectively.

Where a laser beam is irradiated while the pulse intensity is increased stepwise as seen in FIG. 3, for example, if a fine particle is qualified with three different fluorescent dyes, then such four spectra as illustrated in FIGS. 4A to 4D are obtained. Among the detection spectra, the detection spectrum A (laser intensity: Pw1) illustrated in FIG. 4A exhibits an output level substantially equal to a noise level. Meanwhile, in the detection spectrum B (laser intensity: Pw2) illustrated in FIG. 4B, the output power of a channel which exhibits the lowest output power level is substantially equal to a noise level. In the detection spectrum D (laser intensity: Pw4), the output power of a channel which exhibits the highest output level reaches a saturation level. On the other hand, in the detection spectrum C (laser intensity: Pw3) shown in FIG. 4C, the signal level is sufficiently high at all channel outputs. Thus, it is considered that, from among the four detection spectra obtained, the detection spectrum C is most suitable for data analysis and also for fluorescent correction which is carried out prior to the data analysis as occasion demands.

Therefore, in the detection method of the present embodiment, from among detection spectra or the like obtained, an optimum one is selected to carry out data analysis, and a type or a state of the fine particle is identified from a histogram or the like obtained by the data analysis. In particular, where the fine particle is a cell or a bead, the size, shape, internal state, surface state, surface antibody reaction and so forth of the fine particle can be identified.

It is to be noted that the comparison method of detection spectra is not limited to the method which depends upon the output value, but otherwise, detection spectra may be compared, for example, in terms of the signal to noise ratio (SNR) of the output values to select an optimum detection spectrum.

Figure 5:
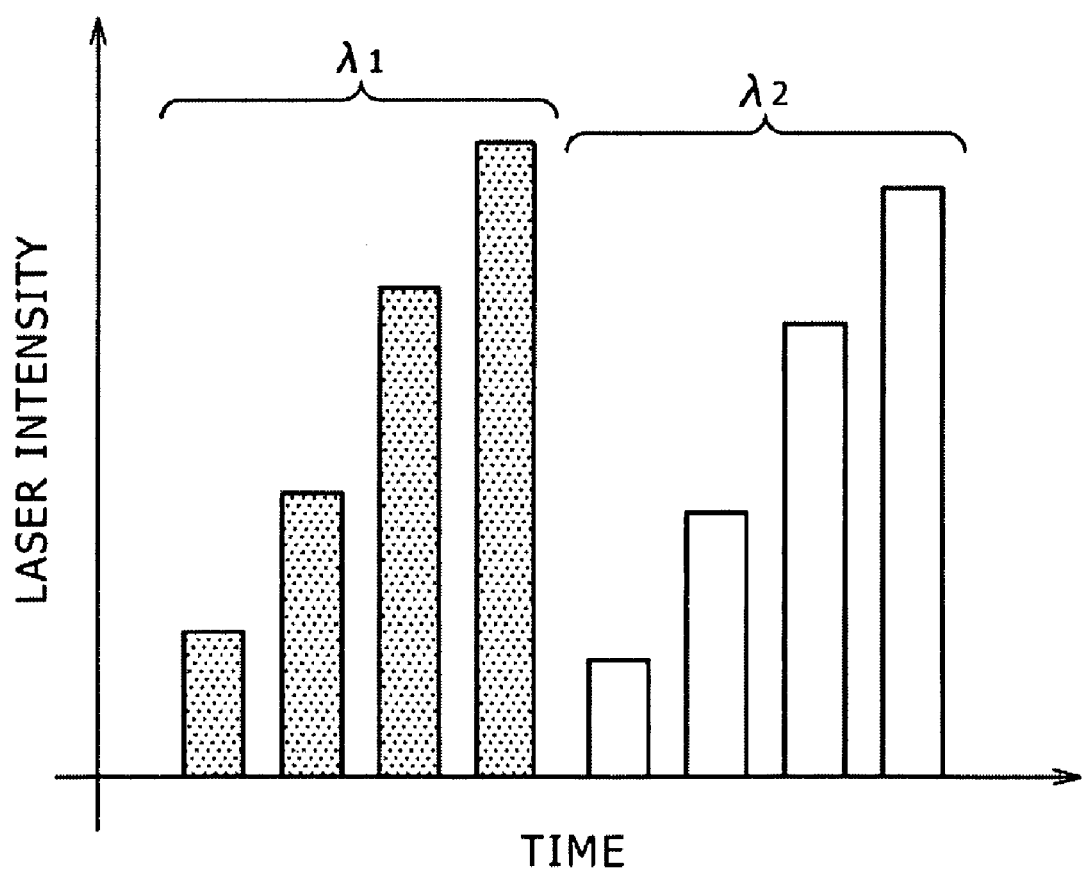
FIG. 5 is a graph illustrating an example of an irradiation pattern where two different laser beams having different wavelengths from each other are irradiated.

FIG. 5 shows a graph wherein the axis of abscissa indicates the time and the axis of ordinate indicates the intensity and illustrates an example of an irradiation pattern where two different laser beams of different wavelengths are irradiated. In the detection method of the present embodiment, also it is possible to irradiate two or more laser beams of different wavelengths. Also it is possible, for example, to first irradiate a pulse laser beam whose wavelength is λ1 while the pulse intensity of the same is modulated and then irradiate another pulse laser beam whose wavelength is λ2 while the pulse intensity of the same is modulated as seen in FIG. 5.

On the other hand, when data analysis is carried out, preferably the detection value of the fluorescent light and/or scattered light 10 is normalized with the intensity of the laser beam 5. In particular, a data processing section not shown is provided in the optical detection apparatus 1 and carries out, for example, a process of normalizing the fluorescent light and/or scattered light 10 detected by the detection section 9 based on the intensity of the laser beam 5.

By normalizing the detection value of the fluorescent light and/or scattered light 10 with the laser intensity upon detection in this manner, absolute value comparison of the fluorescent light intensity can be carried out with regard to a plurality of kinds of fine particles having different optimum laser intensities. As a result, by comparing fluorescent light intensities, for example, comparison in antibody reaction of cells, absolute value comparison in surface reaction of beads and like comparison can be carried out.

As described above, in the optical detection method of fine particles of the present embodiment, since a laser beam of the same wavelength is irradiated upon one fine particle by a plural number of times with the intensity thereof varied, a plurality of detection spectra having different output powers are obtained. Therefore, by selecting an optimum level spectrum from among the detection spectra to carry out data analysis, the detection accuracy can be enhanced even where the difference in luminance level of fluorescent light and/or scattered light emitted from fine particles of a target of detection is great.

Further, in the detection method of the present embodiment, since a pulse laser beam is irradiated upon fine particles, the damage to be applied to fine particles can be reduced and heat generation of fine particles can be suppressed when compared with a related-art detection method wherein a laser beam is always irradiated upon fine particles.

Now, a method of optically detecting a fine particle qualified with two or more different fluorescent dyes as a second embodiment of the present invention is described. For example, where a fine particle is qualified with two or more fluorescent dyes having excitation wavelengths different from each other, it is necessary to irradiate two or more laser beams having different wavelengths from each other upon the fine particle. Therefore, in the present embodiment, two or more pulse lasers having wavelengths λ different from each other are irradiated from the light irradiation section 4 of the optical detection apparatus 1 upon a fine particle with phases thereof displaced from each other while the pulse intensity is modulated.

Figure 6:
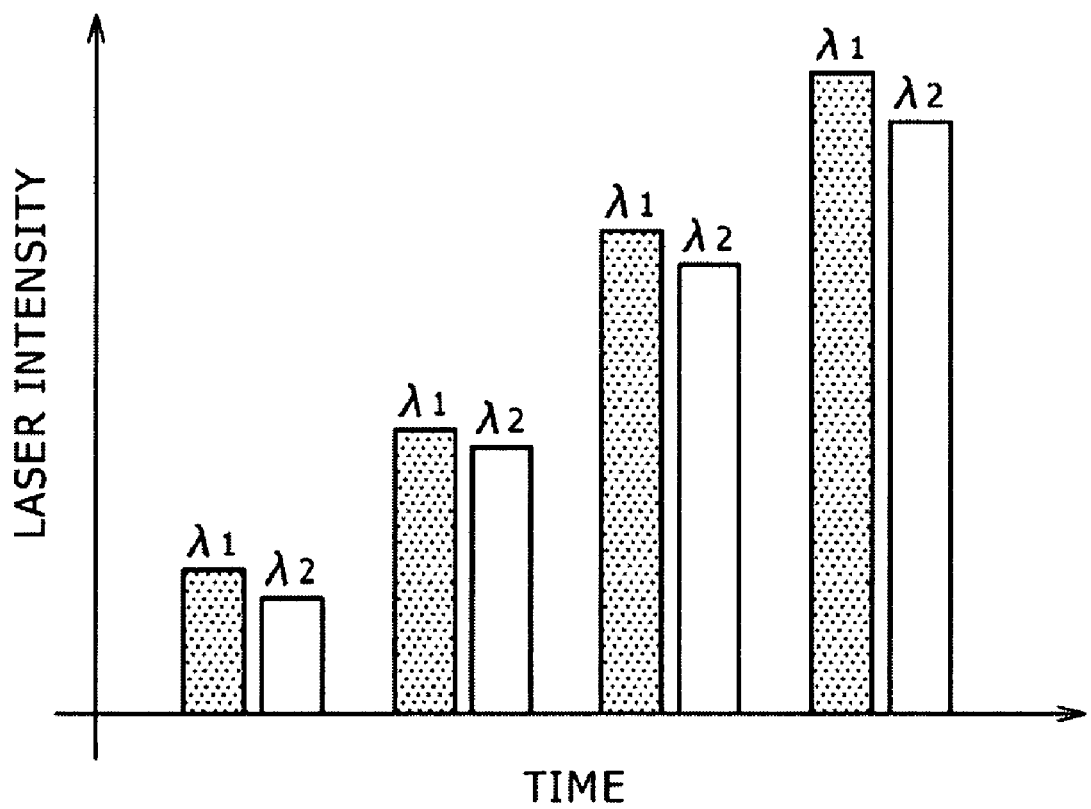
FIG. 6 is a graph illustrating an example of an irradiation pattern of laser beams in an optical detection method according to a second embodiment of the present invention.

FIG. 6 shows a graph wherein the axis of abscissa is the time and the axis of ordinate is the intensity and illustrates an example of an irradiation pattern of laser beams according to the optical detection method of the present embodiment. Referring to FIG. 6, in the detection method of the present embodiment, a plurality of laser beams having different wavelengths from each other are time-divisionally irradiated upon a fine particle while the pulse intensity is modulated for each wavelength. Then, the detection section detects, for each of the wavelengths of the laser beams, fluorescent and/or scattered light irradiated from each fine particle.

In the related-art detection method, a detection fluorescent light signal must be corrected because a plurality of laser beams are irradiated simultaneously. However, in the optical detection method for fine particles in the present embodiment, since two or more laser beams having different wavelengths from each other are irradiated with phases thereof displaced from each other and the intensity of fluorescent and/or scattered light generated from a fine particle is detected for each of the wavelengths of the laser beams, a light detection signal corresponding to a single laser light beam is obtained. As a result, a fluorescent light correction process hereinafter described is facilitated, and the light intensities can be separated in high accuracy.

In the optical detection method of the present embodiment, where a fine particle is qualified with two or more fluorescent dyes and two or more fluorescent dyes from among the fluorescent dyes are excited with one wavelength, it is necessary to carry out fluorescent light correction of separating obtained detection spectra for each fluorescent dye. It is to be noted that, where fine particles are qualified with only one fluorescent dye or only one fluorescent dye is excited by one wavelength, since no leaking in of fluorescent light occurs, the fluorescent light correction process described is not required.

Figure 4A:
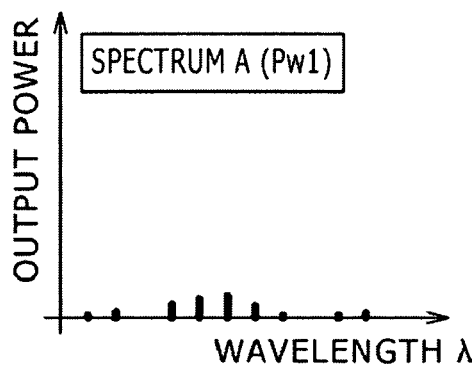
FIGS. 4A to 4D are graphs illustrating detecting spectra obtained when laser beams are irradiated in the irradiation pattern illustrated in FIG. 3.
Figure 4B:
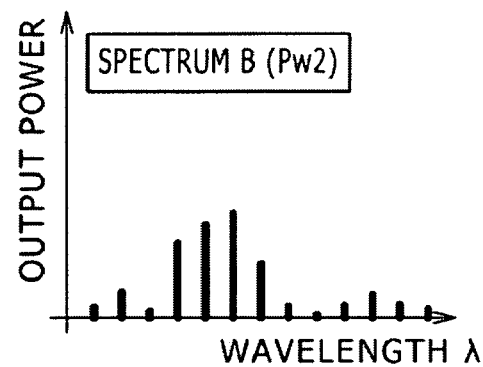
Figure 4C:
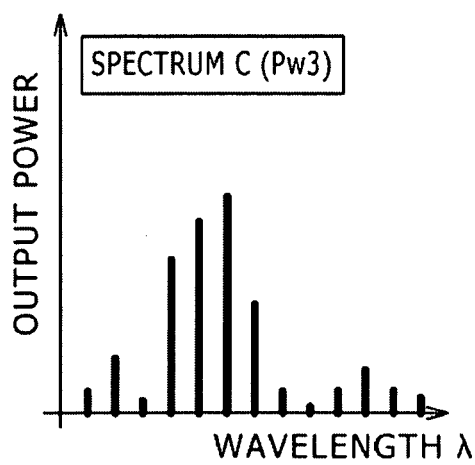
Figure 4D:
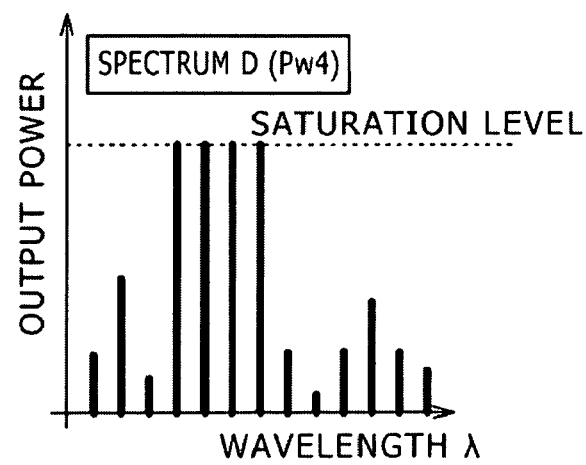
Figure 7A:
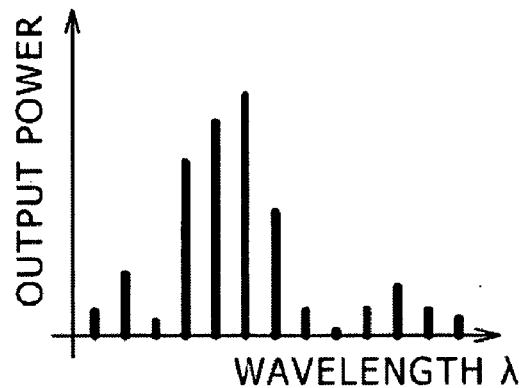
FIGS. 7A to 7C are graphs illustrating a fluorescent light correction process of detection spectra in the order of steps.
Figure 7B:
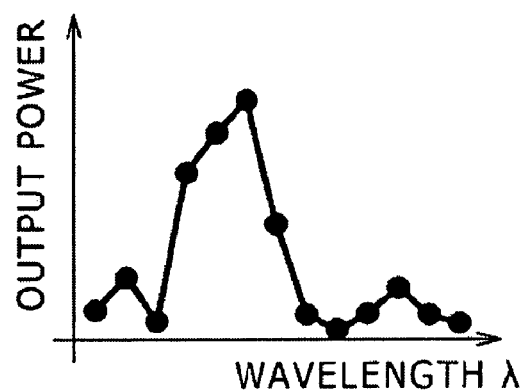
Figure 7C:
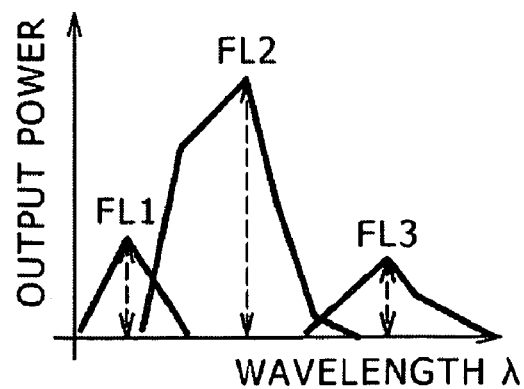

FIGS. 7A to 7C show graphs wherein the axis of abscissa indicates the wavelength and the axis of ordinate indicates the output power and illustrate a fluorescent light correction process for detection spectra in accordance with the order of steps. When fluorescent light correction of detection spectra is to be carried out, first a detection spectrum optimum for fluorescent light correction is selected from among a plurality of detection spectra of different laser intensities as seen in FIG. 7A. For example, if such detection spectra as seen in FIGS. 4A to 4D are obtained, then the detection spectrum C illustrated in FIG. 4C is selected.

Then, a wavelength distribution analysis of the detection spectrum C is carried out based on reference spectra of the individual fluorescent dyes by which the fine particles 3 are qualified as seen in FIG. 7B. Further, a mathematic operation process, that is, an inverse matrix analysis, which utilizes such an inverse matrix as indicated by the following expression (3):

$$\begin{bmatrix} FL_1 \\ FL_2 \\ \vdots \\ \vdots \\ FL_n \end{bmatrix} = \begin{bmatrix} a_1 & a_2 & a_3 & \ldots & a_n \\ b_1 & b_2 & b_3 & \ldots & b_n \\ \vdots & \vdots & \vdots & \vdots & \vdots \\ \vdots & \vdots & \vdots & \vdots & \vdots \\ z_1 & z_2 & z_3 & \ldots & z_n \end{bmatrix}^{-1} \begin{bmatrix} PMT_1 \\ PMT_2 \\ \vdots \\ \vdots \\ PMT_n \end{bmatrix} \quad (3)$$

is carried out to calculate the amounts or proportions of the individual fluorescent lights. It is to be noted that, in the expression (3) above, $FL_n$ is the amount or proportion of each fluorescent dye, $a_n, b_n, c_n, \ldots, z_n$ are the proportions of the wavelengths for each fluorescent dye, and $PMT_n$ is an estimated output value for each wavelength.

Then, the detection spectrum C is decomposed into intensities of the individual fluorescent dyes based on a result of the inverse matrix analysis described above as seen in FIG. 7C. It is to be noted that FIG. 7C illustrates decomposition of a detection spectrum where fine particles are qualified with three different fluorescent dyes for the individual dyes.

Then, data analysis is carried out using the spectra decomposed for the individual dyes by this fluorescent light correction, and the type or state of the fine particle is identified from a histogram or the like obtained by the data analysis. In this instance, preferably the values obtained by the inverse matrix analysis are normalized with the intensity of the laser beam 5. In particular, a data processing section not shown is provided in the optical detection apparatus 1 such that it executes, for example, a process of decomposing the values of the fluorescent light and/or scattered light 10 detected by the detection section 9 for the individual fluorescent dyes by the inverse matrix analysis and then normalizing the resulting values based on the intensity of the laser beam 5. An example of such normalization based on the laser intensity is indicated in Table 1 below:

TABLE 1

| Fine particle No. | Optimum laser intensity (mW) | Value by inverse matrix analysis | | | Value after normalization | | |
|---|---|---|---|---|---|---|---|
| | | Fluorescent dye 1 | Fluorescent dye 2 | Fluorescent dye 3 | Fluorescent dye 1 | Fluorescent dye 2 | Fluorescent dye 3 |
| 1 | Pw2 | FL1a | FL2a | FL3a | FL1a/Pw2 | FL2a/Pw2 | FL3a/Pw2 |
| 2 | Pw4 | FL1b | FL2b | FL3b | FL1b/Pw4 | FL2b/Pw4 | FL3b/Pw4 |
| 3 | Pw3 | FL1c | FL2c | FL3c | FL1c/Pw3 | FL2c/Pw3 | FL3c/Pw3 |
| ... | ... | ... | ... | ... | ... | ... | ... |

By normalizing values obtained by the inverse matrix analysis of fluorescent light intensity levels with the laser intensity upon detection in this manner, also where fine particles having different optimum laser intensities are involved, absolute value comparison of received light intensities can be carried out.

It is to be noted that, in the fluorescent light correction process described above, when inverse matrix analysis of fluorescent light detected when one laser beam is irradiated is to be carried out, a reference spectrum of any fluorescent dye which is not excited by the laser beam may be regarded as zero in the calculation. In particular, where four different fluorescent dyes including fluorescent dyes a and d which are excited by a laser beam α, another fluorescent dye b which is excited by another laser beam β and a further fluorescent dye c which is excited by a further laser beam γ are used for qualification of fine particles, three laser beams α, β and γ having different wavelengths are time-divisionally irradiated while fluorescent and/or scattered light emitted from the fine particles is detected for each of the wavelengths of the laser beams to carry out a fluorescent light correction process.

Figure 8:
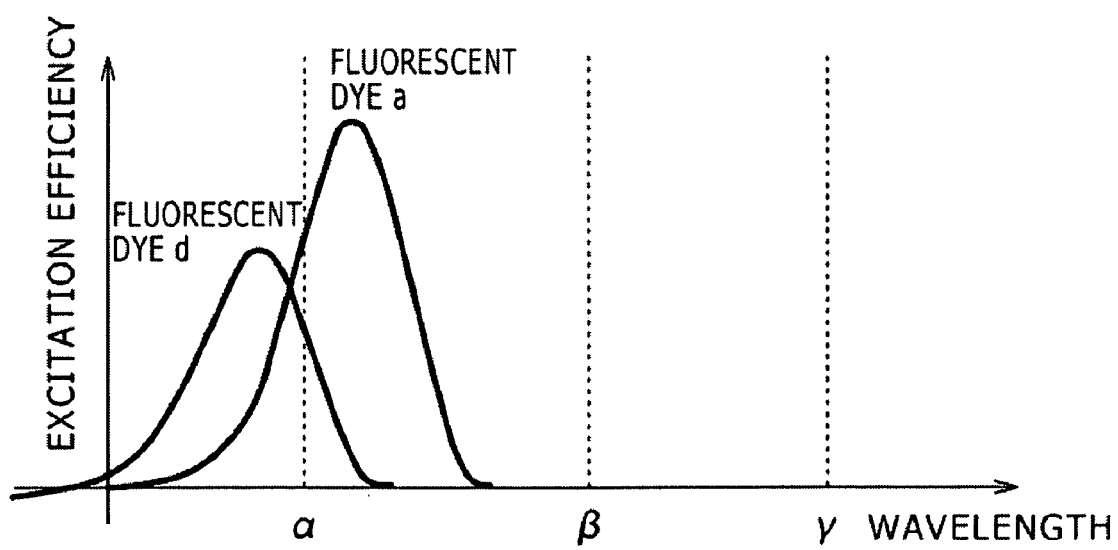
FIG. 8 is a diagram illustrating excitation wavelengths of different fluorescent dyes.

FIG. 8 shows a graph wherein the axis of abscissa indicates the wavelength and the axis of ordinate indicates the excitation efficiency and illustrates excitation wavelengths of the fluorescent dye a and the fluorescent dye d. If the laser beam α is irradiated, then the two different fluorescent dyes of the fluorescent dye a and the fluorescent dye d are excited. Therefore, it is necessary to carry out a fluorescent light correction process for a light detection signal when the laser beam a is irradiated, and thereupon, reference spectra of the fluorescent dye a and the fluorescent dye d may be used while the matrix items of the reference spectra regarding the fluorescent dye b and the fluorescent dye c are set to zero as indicated by the expression (4) given below to carry out the inverse matrix analysis.

$$\begin{bmatrix} y_1 \\ y_2 \\ \vdots \\ y_n \end{bmatrix} = \begin{bmatrix} a_{11} & a_{12} & \ldots & a_{1n} \\ 0 & 0 & \ldots & 0 \\ 0 & 0 & \ldots & 0 \\ d_{11} & d_{12} & \ldots & d_{1n} \end{bmatrix} \begin{bmatrix} x_1 \\ x_2 \\ \vdots \\ x_n \end{bmatrix} \quad (4)$$

where $y_1$ to $y_n$ are light detection signals for the individual wavelengths when the laser beam α is irradiated, $a_{11}$ to $a_{1n}$ reference spectra of the fluorescent dye a for the individual wavelengths, $d_{11}$ to $d_{1n}$ reference spectra of the fluorescent dye d for the individual wavelengths, and $x_1$ to $x_n$ the amounts or proportions of the individual fluorescent dyes.

In this manner, when a fluorescent light correction process is to be carried out, if only the reference spectra of fluorescent dyes excited by different laser light beams are used while the reference spectra of the other fluorescent dyes are set to zero to carry out inverse matrix analysis, then the calculation time can be reduced significantly. As a result, even where fine particles are colored in multiple colors, detection and analysis in short time can be achieved.

It is to be noted that the configuration and the effect of the other part than that described above of the optical detection method of the present embodiment are similar to those of the detection method of the first embodiment described hereinabove.

Now, an optical detection method according to a third embodiment of the present invention is described. The detection method of the present embodiment is similar to the detection methods of the first and second embodiments described hereinabove except that an ultrashort pulse laser beam of a comb shape (hereinafter referred to as comb-like pulse) is used for laser beams to be irradiated from the light irradiation section.

Figure 9A:
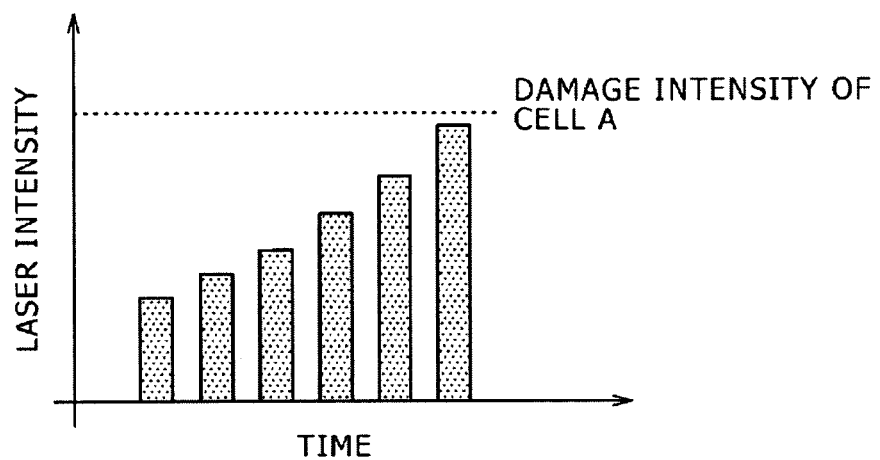
FIGS. 9A and 9B are graphs illustrating irradiation patterns when a comb-like pulse laser beam is irradiated upon different cells having different damage intensities.
Figure 9B:
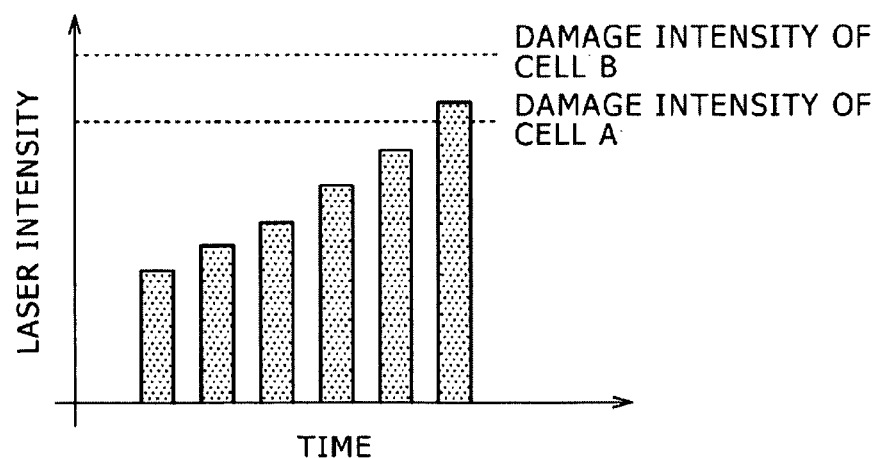
Figure 10A:
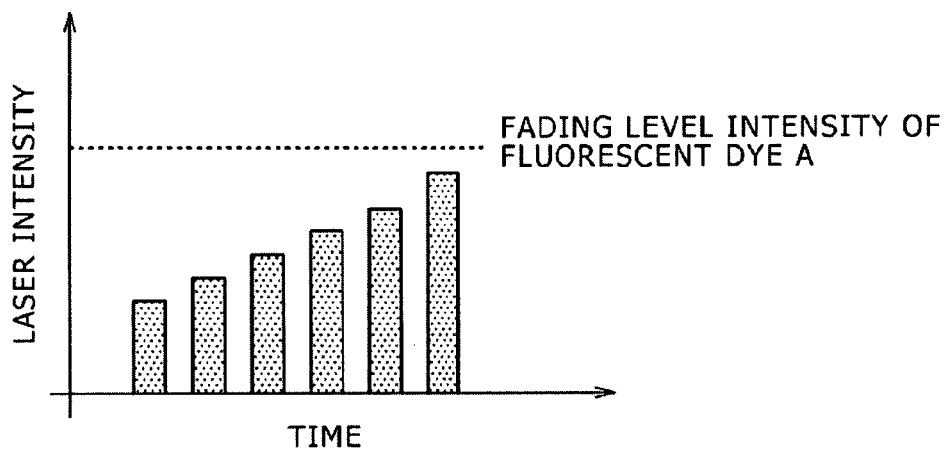
FIGS. 10A and 10B are graphs illustrating irradiation patterns when a comb-like pulse laser beam is irradiated upon fine particles qualified with different fluorescent dyes having different fading level intensities.
Figure 10B:
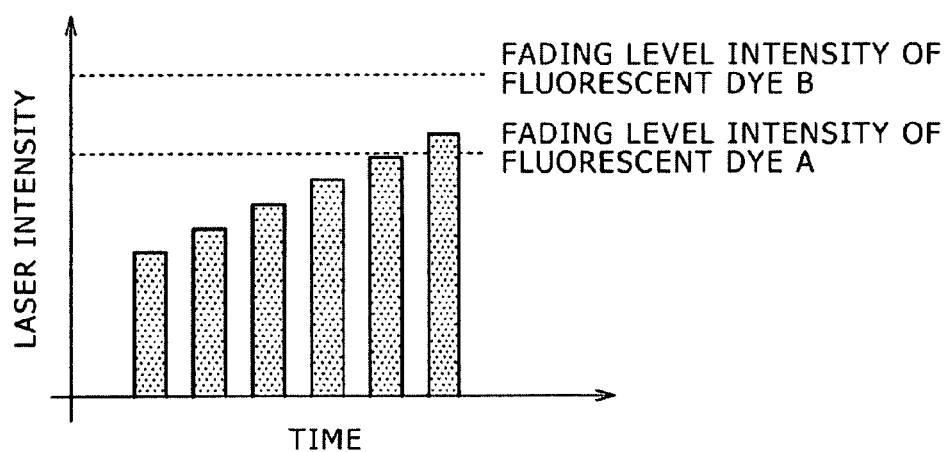
Figure 11:
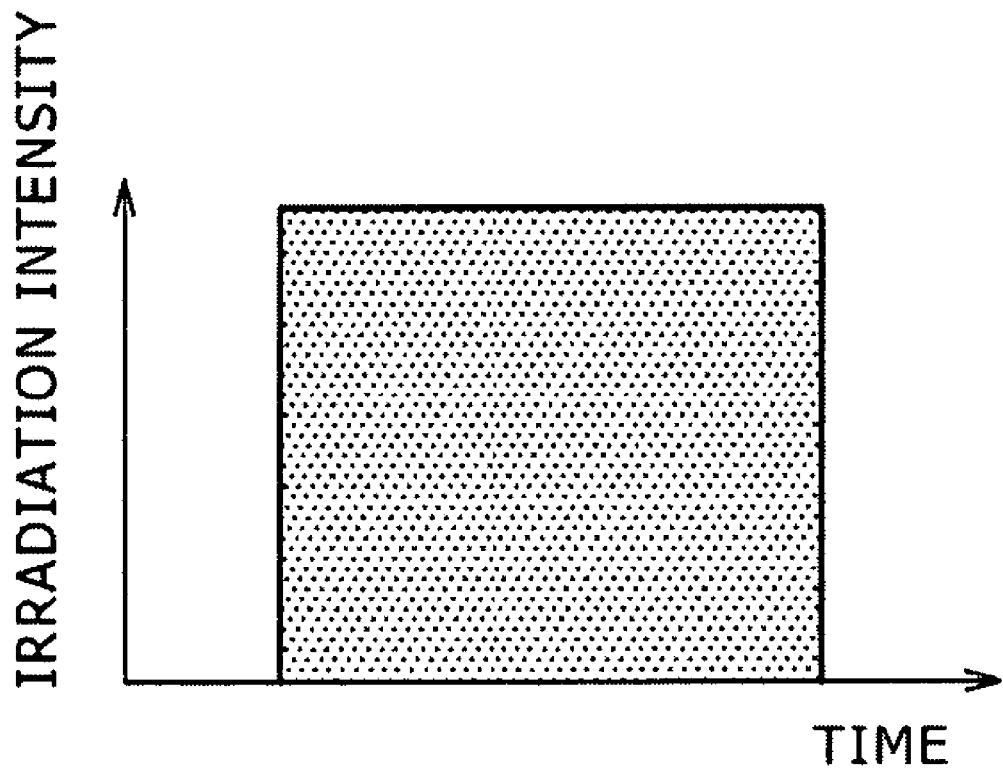
FIG. 11 is a graph illustrating a related-art laser beam irradiation pattern.
Figure 12:
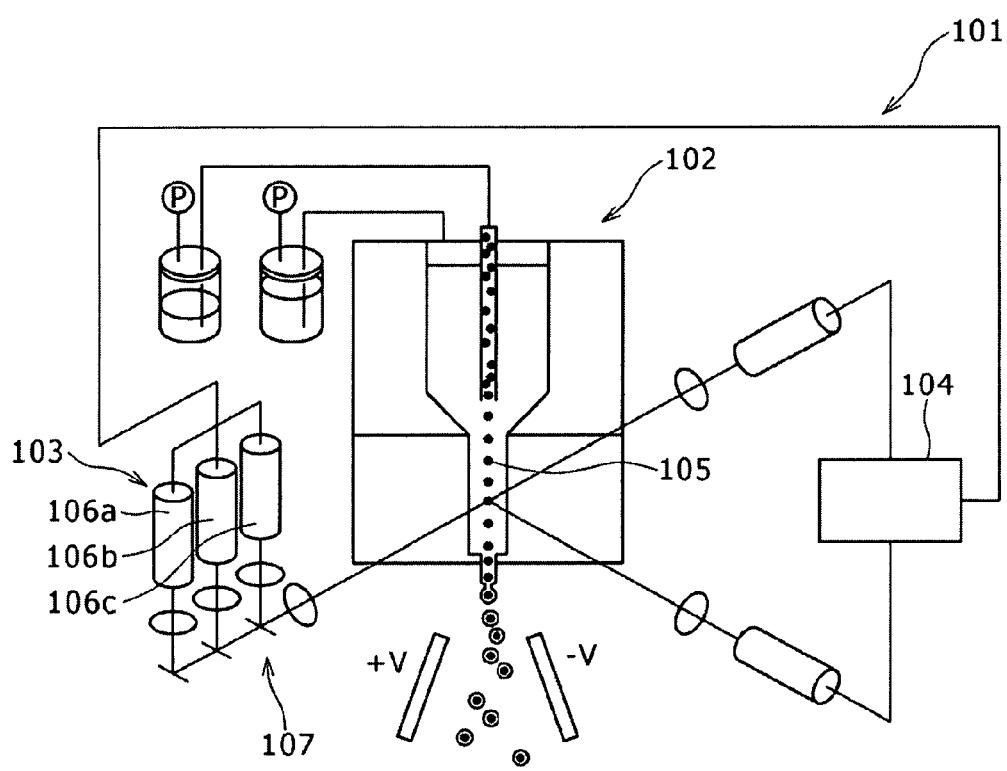
FIG. 12 is a schematic view generally showing a configuration of a related-art flow cytometer disclosed in Patent Document 1.

FIGS. 9A and 9B show irradiation patterns when a comb-like pulse laser beam is irradiated upon a cell A and another cell B which have different damage intensities, respectively. Meanwhile, FIGS. 10A and 10B show irradiation patterns when a comb-like pulse laser beam is irradiated upon fine particles qualified with a fluorescent dye A and another fluorescent dye B having different color fading level intensities. Further, FIG. 11 shows a related-art laser beam irradiation pattern. As seen in FIGS. 9A to 10B, in the detection method of the present embodiment, since the laser beam to be irradiated upon a fine particle is formed as a comb-like pulse laser beam, the total light amount of the laser bean to be irradiated for detecting fluorescent light and scattered light can be reduced in comparison with that by the detection method wherein a laser beam is irradiated continuously as seen in FIG. 11.

Consequently, light damage to fine particles and temperature rise of fine particles can be reduced without deteriorating the light emission intensity of fluorescent or scattered light to be generated from a fine particle. Therefore, fine particles can be dispensed while keeping a state thereof without suffering from degeneration.

Further, in the detection method of the present embodiment, such conditions as the irradiation intensity, irradiation time, irradiation waveform, pulse duration, phase, pulse width and pulse shape may be adjusted in response to a result of detection carried out in advance to detect the temperature and/or the light intensity with which fine particles of an object of detection are destroyed.

The temperature and the light intensity with which fine particles of a detection object are destroyed can be detected using a thermostatic bath and a light irradiation apparatus or the like, respectively. Or, the apparatus of the present invention may be used to measure the survival rate of cells and/or the color deterioration degree of fluorescent beads when the pulse irradiation conditions described above are varied. For example, as regards cells, if the temperature becomes approximately 40 degrees or higher, then thermal damage is applied to the cells and the survival rate of the cells after the detection is low.

Further, for example, if the fine particles of an object of detection are cells, then preferably such conditions are set such that, for example, the irradiation intensity is several mW to several hundreds mW, that the irradiation time is several ns to several ms, that the irradiation waveform is a comb-like pulse waveform and that the pulse duration is several % to several tens %.

By adjusting the conditions of the irradiation intensity, irradiation time, irradiation waveform, pulse duration, phase, pulse width, pulse shape and so forth of the comb-like pulse laser beam in response to the temperature and the light intensity with which fine particles of an object of detection are destroyed in this manner, dropping of a fluorescent dye which qualifies fine particles and color fading of fine particles, which make problems in the past, can be prevented. It is to be noted that all of such irradiation conditions as described above need not be adjusted, but at least one of such irradiation conditions may be adjusted to achieve the effect described above.

Further, the detection method of the present embodiment can be implemented by irradiating one comb-like pulse laser beam or two or more comb-like pulse laser beams of different wavelengths illustrated in FIGS. 9A and 9B or FIGS. 10A and 10B, for example, from the light irradiation section 4 of the optical detection apparatus 1 shown in FIG. 1.

Further, in this instance, preferably the optical detection apparatus 1 includes a database not shown in which detection results of the temperature and/or the light intensity with which various fine particles 3 are destroyed are stored, and a laser beam control section not shown for adjusting at least one of the conditions of the irradiation intensity, irradiation time, irradiation waveform, pulse duration, phase, pulse width and pulse shape of the comb-like pulse laser beam based on a detection result stored in the database. With the optical detection apparatus 1, dropping of a fluorescent dye which qualifies fine particles and color fading of fine particles can be prevented. It is to be noted that the database and the laser light control section need not necessarily be provided in the optical detection apparatus 1.

As described above, with the optical detection method of the present embodiment, since the laser beam to be irradiated upon a fine particle of an object of detection is formed as a comb-like pulse laser beam, the light reception amount and the temperature rise of the fine particle can be reduced thereby to reduce damage to the fine particle and degeneration of the fine particle. The detection method of the present embodiment is particularly effective where fine particles which are liable to degenerate such as cells are detected.

It is to be noted that the configuration and the effect of the other part than that described above of the optical detection method of the present embodiment are similar to those of the detection method of the first and second embodiments described hereinabove.

While preferred embodiments of the present invention have been described using specific terms, such description is for illustrative purpose only, and it is to be understood that changes and variations may be made without departing from the spirit or scope of the following claims.

What is claimed is:

1. An optical detection method, comprising the steps of:
    irradiating two or more laser beams having different wavelengths upon one of fine particles which are successively fed in a flow path; and
    detecting fluorescent light and/or scattered light generated from the fine particle for each of the wavelengths of the laser beams; wherein
    the laser beams are formed as pulse laser beams whose pulse intensity is modulated and whose phases are displaced from each other, wherein the laser beams are irradiated a plural number of times upon one fine particle with the intensity varied.

2. The optical detection method according to claim 1, wherein, where the flow speed of the fine particles is represented by x (m/second), the spot diameter of each laser beam by y (m), the number of times of modulation of each laser beam by w (times) and the number of wavelengths of each laser beam by n, the pulse width p (second) of each laser beam satisfies the following expression (A):

$$p < \frac{y}{x \times (w+1) \times n}. \tag{A}$$

3. The optical detection method according to claim 1, wherein the detected fluorescent light and/or scattered light is normalized based on the intensity of the laser beams.

4. The optical detection method according to claim 3, wherein the type or state of the fine particle is identified from the normalized value.

5. The optical detection method according to claim 1, wherein the fine particles are in a form qualified with two or more different fluorescent dyes, and fluorescent light or scattered light detected when one of the laser beams is irradiated is analyzed by inverse matrix analysis wherein a reference spectrum of any one of the fluorescent dyes which is not excited by the one laser beam is set to zero.

6. The optical detection method according to claim 1, wherein the laser beams are ultrashort pulse laser beam beams.

7. The optical detection method according to claim 6, further comprising the step of detecting a temperature and/or a light intensity with which fine particles of an object of detection are destroyed in advance, at least one of conditions of an irradiation intensity, irradiation time, an irradiation waveform, a pulse duration, a phase, a pulse width and a pulse shape of the pulse laser beams being adjusted in response to a result of the detection.

8. The optical detection method according to claim 1, wherein the fine particles are cells or micro beads.

9. An optical detection apparatus, comprising:
    a light irradiation section configured to irradiate two or more laser beams having different wavelengths upon one of fine particles which are successively fed in a flow path; and
    a light detection section configured to detect fluorescent light and/or scattered light generated from any of the fine particles upon which the laser beams are irradiated for each of the wavelengths of the laser beams;
    said light irradiation section irradiating the laser beams as pulse laser beams while modulating the pulse intensity of the laser beams, with the phases of the laser beams displaced from each other, wherein the laser beams are irradiated a plural number of times upon one fine particle with the intensity varied.

10. The optical detection apparatus according to claim 9, wherein, where the flow speed of the fine particles is represented by x (m/second), the spot diameter of each laser beam by y (m), the number of times of modulation of each laser beam by w (times) and the number of wavelengths of each laser beam by n, the pulse width p (second) of each laser beam satisfies the following expression (A)

$$p < \frac{y}{x \times (w+1) \times n}. \quad (A)$$

11. The optical detection apparatus according to claim 9, further comprising a data processing section configured to normalize the detected fluorescent light and/or scattered light based on the intensity of the laser beams.

12. The optical detection apparatus according to claim 11, wherein the type or state of the fine particle is identified from the normalized value.

13. The optical detection apparatus according to claim 9, wherein, where the fine particles are in a form qualified with two or more different fluorescent dyes, fluorescent light or scattered light detected when one of the laser beams is irradiated is analyzed by inverse matrix analysis wherein a reference spectrum of any one of the fluorescent dyes which is not excited by the one laser beam is set to zero.

14. The optical detection apparatus according to claim 9, wherein the laser beams are ultrashort pulse laser beams.

15. The optical detection apparatus according to claim 14, further comprising a laser beam control section configured to adjust, based on data detected in advance of a temperature and/or a light intensity with which fine particles of an object of detection detected are destroyed, at least one of conditions of an irradiation intensity, irradiation time, an irradiation waveform, a pulse duration, a phase, a pulse width and a pulse shape of the pulse laser beams.

16. The optical detection apparatus according to claim 9, wherein the fine particles are cells or micro beads.

* * * * *